United States Patent [19]

Ueda et al.

[11] Patent Number: 4,594,429
[45] Date of Patent: Jun. 10, 1986

[54] PROCESS FOR PRODUCING THE 3-CHLORO-1-FORMYL-4-PHENYLPYRROLES

[75] Inventors: Akiyoshi Ueda; Fumihiko Nagasaki; Yutaka Takakura; Shigeru Kojima, all of Kanagawa, Japan

[73] Assignee: Nippon Soda Co. Ltd., Tokyo, Japan

[21] Appl. No.: 619,158

[22] PCT Filed: Oct. 21, 1983

[86] PCT No.: PCT/JP83/00371
§ 371 Date: Jun. 4, 1984
§ 102(e) Date: Jun. 4, 1984

[87] PCT Pub. No.: WO84/01773
PCT Pub. Date: May 10, 1984

[30] Foreign Application Priority Data

Oct. 28, 1982 [JP] Japan .................. 57-188191
Oct. 28, 1982 [JP] Japan .................. 57-188192

[51] Int. Cl.[4] ........................................... C07D 207/30
[52] U.S. Cl. ............................... 548/530; 548/565
[58] Field of Search ................... 548/530, 565

[56] References Cited

U.S. PATENT DOCUMENTS 3,644,374 2/1972 Buijle et al. .................. 548/530 X
4,303,667 12/1981 Ueda et al. .................. 548/530 X

*Primary Examiner*—Joseph D. Brust
*Attorney, Agent, or Firm*—George B. Oujevolk

[57] ABSTRACT

The present invention relates to a novel process for producing 3-chloro-1-formyl-4-phenylpyrroles having the general formula [I] as a useful fungicidal agent in agriculture and horticulture which is manufactured from the starting material of 3-phenyl-2,2,4-trichlorobutanal having the general formula [IV] as set forth in the following reaction formulae:

By means of obtaining a pyrroline derivative having the general formula [III] as the intermediate compound, its production operation is greatly simplified and its yield rate is raised in comparison with the conventional processes.

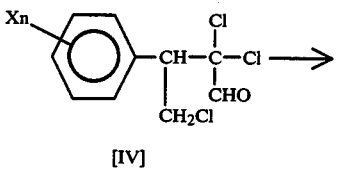

[IV]

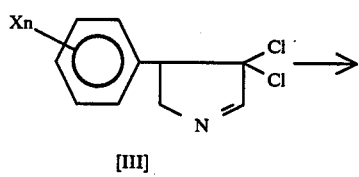

[III]

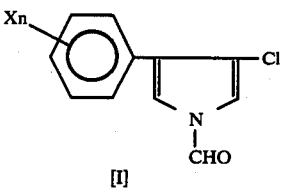

[I]

where X denotes the same or different kinds of substituent(s) being chosen from the group consisting of halo, nitro, and trifluoromethyl and n denotes zero or an integer of 1 or 2.

2 Claims, No Drawings

PROCESS FOR PRODUCING THE 3-CHLORO-1-FORMYL-4-PHENYLPYRROLES

FIELD OF THE INVENTION

The present invention relates to a novel process for producing the 3-chloro-1-formyl-4-phenylpyrrole, as a useful fungicidal agent to agriculture and horticulture, which is represented by the general formula:

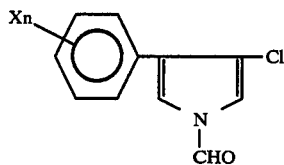
[I]

wherein X denotes the same or different kind(s) of substituted groups being chosen from halogen atom, nitro group and/or trifluoromethyl group and n denotes zero or an integer of 1 or 2.

BACKGROUND OF THE INVENTION

In order to produce the compounds represented by the general formula [I], first a process is used which comprises synthesizing the pyrroles having the general formula [II]:

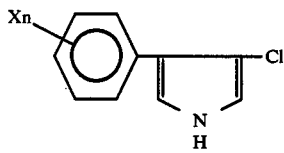
[II]

and then, the compound having the general formula II is treated with a formulating step, as heretofore described in the prior art (U.S. Pat. No. 4,303,667).

In the general formula [II], X and n have the same significances defined above.

Further, as to the process for producing the said pyrroles having the general formula [II], the conventional process is set forth below in which taking into consideration the reactivity of the pyrrole, both α-positions of pyrrole are protected with easily separable protective groups and then its β-position is treated with a chlorination step. This process is well known.

But, those conventional processes utilize numerous procedures and those operations involves difficult steps, so that those processes can not be said to be an industrially desirable method.

(a)

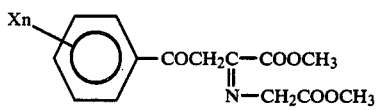

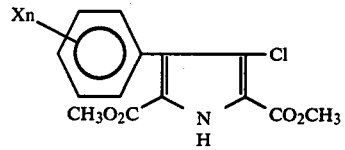

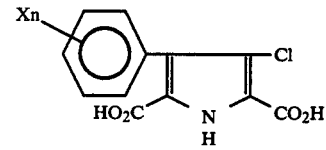

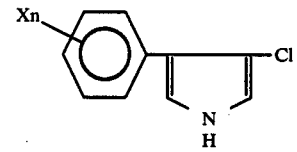

(U.S.P 4236881)

(b)

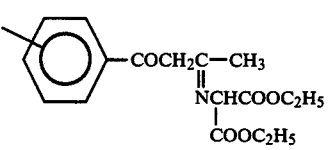

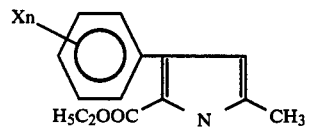

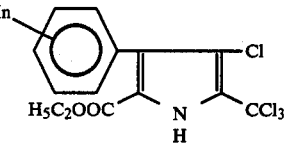

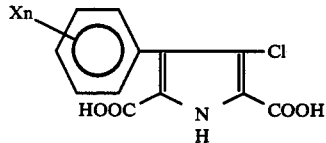

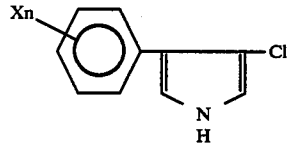

[Chem Pharm Bull 17(3) 582~7 ('69) Ibid 17(3) 588~95('69)]

SUMMARY OF THE INVENTION

The manufacturing process by the present invention is to provide the method set forth in the following reaction formulae which comprises using 3-phenyl-2,2,4-trichlorobutanals as a raw material and obtaining a novel pyrroline derivative having the general formula:

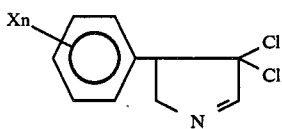

as an intermediate wherein X and n have the same significances defined above.

The said method aims to greatly curtail the production steps and to raise the rate of yield.

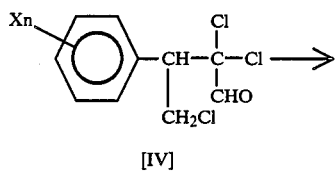

[IV]

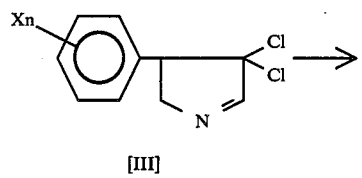

[III]

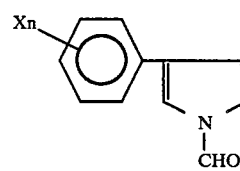

[I]

THE BEST MODE FOR CARRYING OUT THE INVENTION

In carrying out the present invention into practice, the compound having the general formula [IV] is made to react with ammonia gas or aqueous ammonia in an organic solvent at a temperature ranging from room temperature to 50° C., desirably at about 40° C. of temperature and thereby, the pyrroline derivative having the said general formula [III] is produced (the First Step).

Then, the said pyrroline derivative is made to react with a Vilsmeyer reagent in an organic solvent such as dimethylformamide or ethylene dichloride. (The Second Step).

The intermediate reaction compound obtained thereto is hydrolysed in water or an aqueous solution containing sodium acetate or sodium carbonate as the Third Step and thereby, the pyrrole derivative having the general formula [I] is produced.

As the solvent employable for the First Step, an inert solvent involving glyme, dioxane, ethylether, isopropylether, ethanol, propanol, benzene or the like is used, but ethers are desirably used.

As said Vilsmeyer's reagent used in the Second Step, the addition product which consists of one kind or more compound(s) of thionyl chloride, phosphorus oxychloride, oxalylchloride and/or phosgene with formamide derevative(s) involving N,N-dimethylformamide, N-formyl-morpholine or N-methylformamide are used, Desirably, the adduct material of phosphorus oxychloride and N,N-dimethylformamide is used.

As the said organic solvent, ethylene dichloride or chlorobenzene may be used and further by adding a surplus amount of dimethylformamide as the raw material, it may be simultaneously used as the solvent. The reaction is carried out at 70° C. to 125° C.

The usual Vilsmeyer's reaction in the hydrolysis of the Third Step is carried out with the heating and refluxing procedure in an alkaline solution containing sodium carbonate, sodium acetate or the like, but the process of the present invention is desirably carried out in the water or an aqueous alkaline solution at the room temperature.

The resulting hydrolyzed product is extracted with an appropriate organic solvent and it is washed with water and dried and then, the solvent is distilled off and thereby the crude objective material is obtained. Further, if it is necessarily purified, a common purifying operation such as a column chromatography step or recrystallization step is carried out and thereby the desired compound of 3-chloro-1-formyl-4-phenylpyrroles can be obtained.

The compound represented by the general formula [IV] is a novel compound and it can be produced by reacting the diazonium salt of the corresponded aniline with 2,4-dichloro-2-butenal.

In order to give those skilled in the art a better understanding of the invention the following illustrative examples are given:

EXAMPLE 1

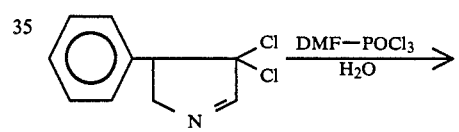

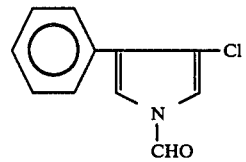

2.95 g (19.2 m mol) of phosphorours oxychloride was gradually added in 10 ml of N,N-dimethylformamide in the ice water cooling step. It was agitated for 20 minutes at room temperature and then, the reactor was cooled again with the ice water and 2.05 g (9.5 m mol) of 3,3-dichloro-4-phenyl-$\Delta^1$-pyrroline was gradually added in it.

The resulting reaction mixture was agitated during 4 hours at 96° C. and then, it was poured into 50 ml of ice water and it was extracted with 50 ml of ethyl acetate.

The resulting extracted solution was washed with water and dried and then it was concentrated and thus, 1.9 g of the crude objective material was obtained.

This crude material was purified with the silicagel-column chromatography method (a solution of benzene: n-hexane=1:1) and thus, 1.64 g of 3-chloro-1-formyl-4-phenylpyrrole was obtained. Yield rate: 83 percent and $n_d^{31}$: 1.6175

EXAMPLE 2

(a) The First Step:

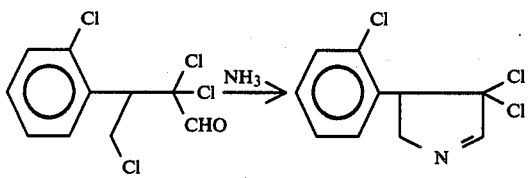

5.0 g of 3-(2-chlorophenyl)-2,2,4-trichlorobutanal was dissolved in 60 ml of glyme and ammonia gas was blown into it during 4 hours at 40° C. and under an agitating step. The resulting sediment was filtered and then, its solvent was distilled off under a reduced pressure.

The residue was dissolved in 70 ml of ether and it was washed with water and then, it was dried.

The hydrogen chloride gas was blown into the said ether solution under the ice water cooling step and the sediment produced was rinsed with the filtered ether and thereby, 3.8 g of 3,3-dichloro-4-phenyl-$\Delta^1$-pyrroline-hydrochloride salt was obtained.

The said hydrochloride salt was suspended in 50 ml of water and the solution, containing saturated sodium hydrogen carbonate was added in it and it was neutralized.

80 ml of ether was added in it and it was extracted and then, it was washed with water and it was dried and its solvent was distilled off and thereby, 2.2 g of 3,3-dichloro-4-(2-chlorophenyl)-$\Delta^1$-pyrroline was obtained.

Yield rate: 51 percent. $n_D^{25}$: 1.5815; 1R (cm$^{-1}$)=1620, 1595, 1570, 1480, 1440.

(b) The Second Step and the Third Step:

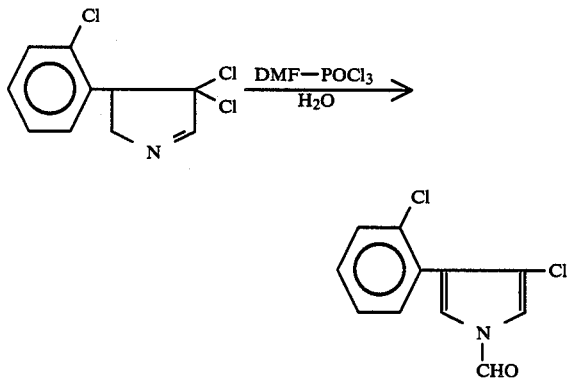

1.48 g (9.6 m mol) of phosphorous oxychloride was gradually added in 5 ml of N,N-dimethylformamide under the ice water cooling step.

It was agitated during 20 minutes at room temperature and then, the reactor was again cooled with the ice water and 1.20 g (4.8 m mol) of 3,3-dichloro-4-(2-chlorophenyl)-$\Delta^1$-pyrroline was gradually added in it.

The reaction mixture was agitated at 96° C. during 7 hours and then, it was treated with the same post treatment as similar as that in the Example 1 and thus, 1.0 g of the crude objective material was obtained.

The said crude objective material was purified with the silicagel column chromatography (the solution of benzene and n-hexane=1:1) and thereby, 0.78 g of 3-chloro-4-(2-chlorophenyl)-1-formylpyrrole was obtained.

Yield rate: 67 percent. Melting point: 72° C. to 74° C.

EXAMPLE 3

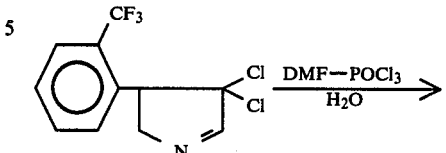

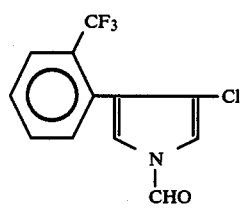

2.58 g (16.8 m mol) of phosphorous oxychloride was gradually added in 9 ml of N,N-dimethylformamide under the ice water cooling step. It was agitated during 15 minutes at room temperature and then, the reactor was again cooled and 2.36 g (8.4 m mol) of 3,3-dichloro-4-(2-trifluorometylphenyl)-$\Delta^1$-pyrroline was gradually added in it.

The resulting solution was agitated during 13 hours at 96° C. and then, it was treated with the same post treating and the purification step as similar as those in Example 1 and thus, 0.80 g of 3-chloro-1-formyl-4-(2-trifluoromethylphenyl)-pyrrole was obtained.

Yield rate: 39 percent. Melting point: 75° C. to 78° C.

EXAMPLE 4

(a) The First Step:

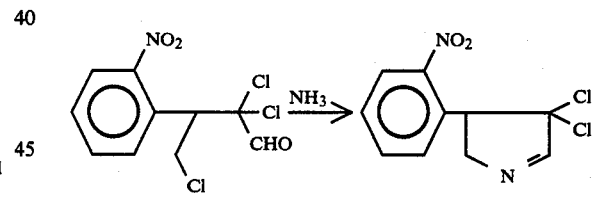

10.0 g of 3-(2-nitrophenyl)-2,2,4-trichlorobutanal was dissolved in 80 ml of glyme and ammonia gas was blown into it during 4 hours at 36° C. and under the agitating step.

It was treated with the same treatment in Example 2 (a) and thus, 5.6 g of 3,3-dichloro-4-(2-nitrophenyl)-$\Delta^1$-pyrrole was obtained.

Yield rate: 64 percent. $n_D^{28}$: 1.5861; 1R (cm$^{-1}$) 1620, 1610, 1580, 1530, 1350.

(b) The Second Step and the Third Step:

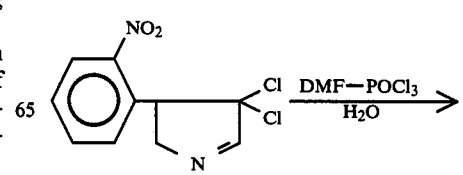

-continued

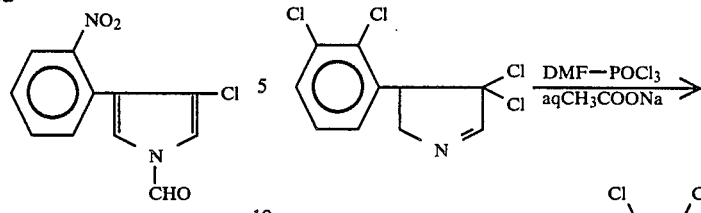

5.09 g (33 m mol) of phosphorous oxychloride was gradually added in 15 ml of N,N-dimethylformamide under the ice water cooling step.

It was agitated during 30 minutes at room temperature and then, the reactor was again cooled and 4.29 g (16.6 m mol) of 3,3-dichloro-4-(2-nitrophenyl)-Δ¹-pyrroline was gradually added in it. It was agitated during 7 hours at 96° C. and it was treated with the same post treatment and purifying step as similar as those in the Example 1 and thus, 2.33 g of 3-chloro-1-formyl-4-(2-nitrophenyl)-pyrrole was obtained.

Yield rate: 56 percent. Melting point: 78.5° C. to 79.5° C.

EXAMPLE 5

(a) The First Step:

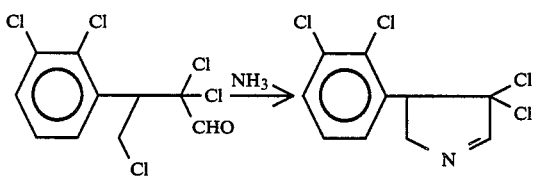

12.8 g of 3-(2,3-dichlorophenyl)-2,2,4-trichlorobutanal was dissolved in 80 ml of glyme and ammonia gas was blown into it during 4 hours at 40° C. and under its agitating step.

The sediment produced was filtered and then, its solvent was distilled off under a reduced pressure.

The residue was dissolved in 200 ml of ether and it was washed with water and dried. Hydrogen chloride gas was blown in the ether solution under the ice water cooling step and the sediment separated was fillered and its ether was rinsed and thus, 12.1 g of 3,3-dichloro-4-(2,3-dichlorophenyl)-Δ¹-pyrroline hydrochloride salt was obtained.

The said hydrochloride salt was suspended in 100 ml of water and the aqueous solution containing saturated sodium hydrogen carbonate was added in it and it was neutralized.

200 ml of ether was added in it and it was extracted and then, it was washed with water and dried and its solvent was distilled off under a reduced pressure and thereby, 10.0 g of 3,3-dichloro-4-(2,3-dichlorophenyl)-Δ¹-pyrroline was obtained.

Yield rate: 88 percent $n_D^{30.5}$: 1.5937 Mass Spectrum: M+=281 IR (cm⁻¹) 1620, 1580, 1560, 1450, 1420 NMR (CDCl₃): δ=3.9 to 4.1 ppm(2H), 4.4 to 4.5 ppm(1H), 6.5 to 7.0 ppm(4H)

(b) The Second Step and the Third Step:

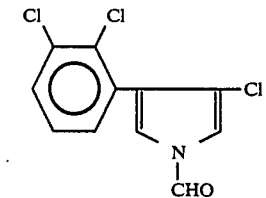

3.08 g (20 m mol) of phosphorous oxychloride was gradually added in 10 ml of N,N-dimethylformamide under the ice water cooling step.

It was agitated at room temperature during 20 hours and then, the reactor was again cooled and 2.80 g (10 m mol) of 3,3-dichloro-4-(2,3-dichlorophenyl)-Δ¹-pyrroline was gradually added it.

It was agitated at 96° C. during 7 hours and then, the reaction solution was poured in the ice water and further an solution containing 8.2 g of sodium acetate was added in it and it was agitated at room temperature during 30 minutes.

It was extracted with 100 ml of ethyl acetate and it was washed with water and dried and then, it was concentrated and thereby, 3.4 g of crude objective material was obtained.

The said crude material was purified with the method of silicagel column chromatograph by using the solution of benzene: n-hexane=1:1 and thus, 2.23 g of 3-chloro-4-(2,3-dichlorophenyl)-1-formylpyrrole was obtained.

Yield rate: 81 percent. Melting point: 129° C. to 130° C.

EXAMPLE 6

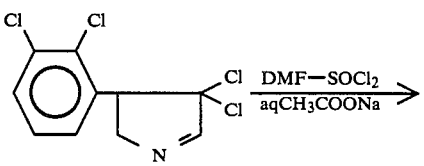

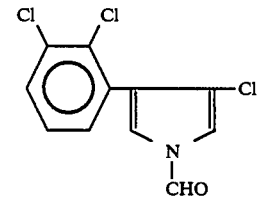

2.4 g (20 m mol) of thionyl chloride was gradually added in 17 ml of N,N-dimethylformamide under the ice water cooling step. It was agitated at room temperature and then, the reactor was again cooled and 2.80 g (10 m mol) of 3,3-dichloro-4-(2,3-dichlorophenyl)-Δ¹-pyrroline was gradually added in it. It was agitated at 85° C. during 7 hours and then, the reaction solution was poured in the ice water and then, the aqueous solution containing 6.6 g of sodium acetate and it was agitated at room temperature during 30 minutes. Hereinafter, it was treated with the same post treatment and purifying step as similar as those in the Example 5 and thus, 1.08 g of 3-chloro-4-(2,3-dichlorophenyl)-1-formylpyrrole was obtained.

Yield rate: 40 percent.

EXAMPLE 7

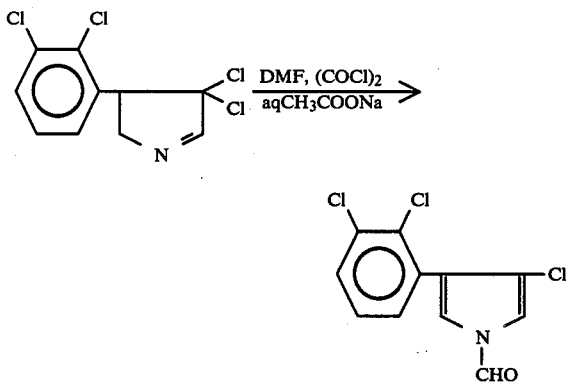

1.3 g (10 m mol) of oxalyl chloride was gradually added in 9 ml of N,N-dimethylformamide under the cooling step with a bath of ice and sodium chloride. It was agitated at the same temperature during 20 minutes and then, 1.40 g (5 m mol) of 3,3-dichlorophenyl-4-(2,3-dichlorophenyl)-$\Delta^1$-pyrroline was gradually added in it.

The resulting mixture was agitated for 14 hours.

The reaction solution was poured in the ice water and then, the aqueous solution containing 3,3 g of sodium acetate was added in it and it was agitated at room temperature during 30 minutes.

Hereinafter, it was treated with the same post treatment and purifying step as similar as those in the Example 5 and thus, 0.71 g of 3-chloro-4-(2,3-dichlorophenyl)-1-formylpyrrole was obtained.

Yield rate: 52 percent.

EXAMPLE 8

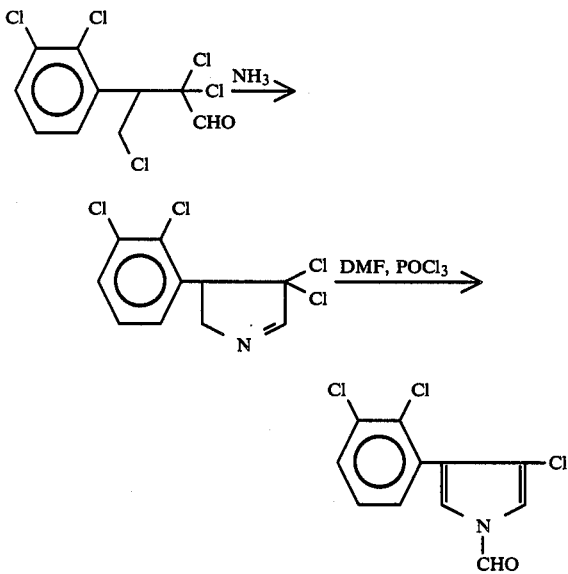

3.2 g of 3-(2,3-dichlorophenyl)-2,2,4-trichlorobutanal was dissolved in 60 ml of glyme and ammonia gas was blown into it at 40° C. during 4 hours under the agitating step.

Its solvent was distilled off under the reduced pressure and the resulting residue was dissolved by adding ether and water and the solution obtained was separated, washed with water and dried.

It was concentrated and thereby, 2.8 g of oily material was obtained.

On the other hand, 3.08 g of phosphorus oxychloride was gradually added in 10 ml of N,N-dimethylformamide and then, it was agitated at room temperature during 20 minutes and thereby Vilsmeyer reagent was prepared.

The oily material obtained before was gradually added in this solvent in the ice water cooling step and then, it was agitated at 96° C. for 7 seven hours.

Then, it was treated with the same post treatment and purifying step as similar as those in Example 5 and thus, 2.03 g of 3-chloro-4-(2,3-dichlorophenyl)-1-formylpyrrole was obtained.

Yield rate: 74 percent

Subsequent, Manufacturing Examples for producing the raw material compound having the general formula [IV] are set forth below:

MANUFACTURING EXAMPLE 1

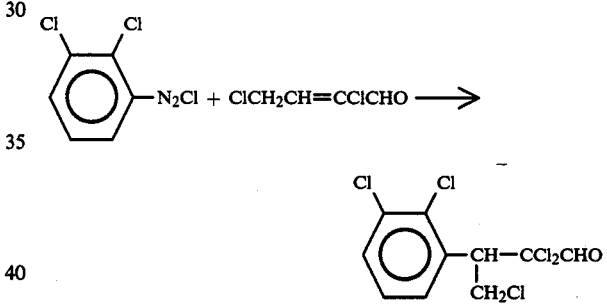

8 ml of water containing 3.8 g of sodium nitrite was dropped in the solution consisting of 8.2 g (0.05 mol) of 2,3-dichloroaniline, 10 ml of water and 15 ml of concentrated hydrochloric acid at 0° C. to 2° C.

It was agitated during 20 minutes and then, after treating it with the filtering step, an aqueous solution containing diazonium salt was obtained.

The mixed solution consisting of 4.7 g (0.033 mol) of 2,4-dichlorocroton aldehyde, 20 ml of acetone and 9.2 g of potassium chloride was added in the said solution of the diazonium salt prepared before at 0° C. to 5° C. Its pH was adjusted to 2 with the aqueous solution containing saturated sodium acetate, and 1.0 g of cupric chloride was added in it and thereby its reaction was carried out at 15° C. to 20° C. during 18 hours.

After having finished the reaction, it was extracted three times with 30 ml of ether and it was washed with water by using the aqueous solution containing saturated sodium chloride and it was dried with magnesium sulfate and then, it was distilled with ether.

The oily material obtained was distilled and thereby, 4.8 g of desired material was obtained.

Yield rate: 45 percent, melting point: 76° C.; boiling point: 140° C. to 148° C./0.3 mmHg.

MANUFACTURING EXAMPLE 2

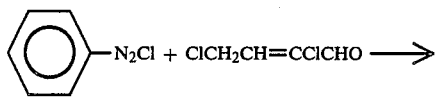

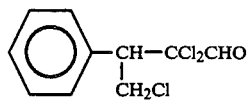

The aqueous solution containing 4 ml of water and 1.3 g of sodium nitrite was dropped in the solution consisting of 1.7 g (0.018 mol) of aniline, 8 ml of water and 6 ml of concentrated hydrochloric acid and by means of the same treatment in the Example 1, the aqueous solution of diazonium salt was prepared.

The said aqueous solution of diazonium salt prepared before was added in the mixed solution consisting of 7.5 g (0.053 mol) of 2,4-dichlorocrotonaldehyde, 18 ml of acetone and 1.9 g of sodium acetate at 0° C. to 5° C.

1.2 g of lithium chloride and 0.35 g of cupric chloride were added in it and its reaction was carried out at 15° C. to 20° C. during 18 hours. The acetone was distilled off from the reaction solution and it was extracted twice with 40 ml of ether and then, the extracted solution was dried with magnesium sulfate and the ether was distilled off. The residual oily material was distilled and thereby, 1.9 g of the objective material was obtained.

Yield rate: 41.4 percent. boiling point: 96° C. to 97° C./0.15 mmHg.

What is claimed is:

1. A process for producing a compound represented by the general formula:

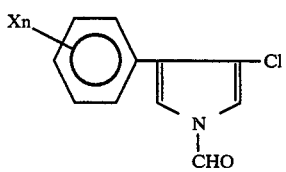

by reacting a pyrroline derivative having the general formula:

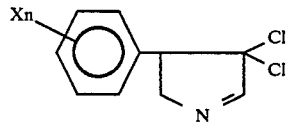

with an addition product consisting of a formamide derivative selected from the group consisting of N,N-dimethylformamide, N-formyl-morpholine and N-methylformamide and a material selected from the group consisting of thionyl chloride, phosphorous oxychloride, oxalyl chloride, phosgene and mixtures thereof at a temperature of between about 70° C. and about 125° C., then hydrolysing the resulting reaction compound at a temperature between about 5° C. and about 100° C., in a solution selected from the group consisting of an aqueous solution and an alkaline solution and obtaining above formulated compound, wherein X denotes substituent(s) selected from the group consisting of halo, nitro and trifluoro methyl and n denotes zero or an integer of 1 or 2.

2. A process for producing the pyrroline derivative claimed in claim 1 which comprises reacting a compound having the general formula:

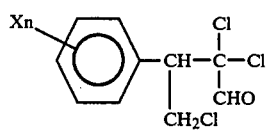

with ammonia gas or aqueous ammonia at a temperature ranging from room temperature to 50° C. and thereby producing the pyrroline derivative represented by the general formula:

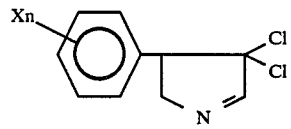

wherein X and n have the same significance as in claim 1.

* * * * *